US012751647B2

(12) United States Patent
Surace

(10) Patent No.: US 12,751,647 B2
(45) Date of Patent: Oct. 6, 2026

(54) POSTUROGRAPHIC EVALUATION APPARATUS AND METHOD

(71) Applicant: CENTRO DI FISIOTERAPIA DI CECILIA SURACE & C. S.A.S., Maglie (IT)

(72) Inventor: Filippo Surace, Maglie (IT)

(73) Assignee: CENTRO DI FISIOTERAPIA DI CECILIA SURACE & C. S.A.S., Maglie (IT)

( * ) Notice: Subject to any disclaimer, the term of this patent is extended or adjusted under 35 U.S.C. 154(b) by 455 days.

(21) Appl. No.: 18/253,537

(22) PCT Filed: Nov. 15, 2021

(86) PCT No.: PCT/IB2021/060552

§ 371 (c)(1),
(2) Date: May 18, 2023

(87) PCT Pub. No.: WO2022/106978

PCT Pub. Date: May 27, 2022

(65) Prior Publication Data

US 2024/0016414 A1 Jan. 18, 2024

(30) Foreign Application Priority Data

Nov. 19, 2020 (IT) ........................ 102020000027774

(51) Int. Cl.

| | |
|---|---|
| ***A61B 5/11*** | (2006.01) |
| ***A61B 5/00*** | (2006.01) |
| ***A61B 5/103*** | (2006.01) |

(52) U.S. Cl.

CPC .......... *A61B 5/1116* (2013.01); *A61B 5/1036* (2013.01); *A61B 5/1126* (2013.01);

(Continued)

(58) Field of Classification Search

CPC ... A61B 5/1116; A61B 5/1036; A61B 5/4023; A61B 5/4561; A61B 5/486

See application file for complete search history.

(56) References Cited

U.S. PATENT DOCUMENTS

| | | | | |
|---|---|---|---|---|
| 9,149,222 B1 | 10/2015 | Zets et al. | | |
| 2002/0193707 A1* | 12/2002 | Atlas | A61B 5/1116 600/595 | |

(Continued)

FOREIGN PATENT DOCUMENTS

| | | |
|---|---|---|
| CN | 101912271 A | 12/2010 |
| JP | 2016041155 A | 3/2016 |
| WO | 2019/232899 A1 | 12/2019 |

OTHER PUBLICATIONS

International Search Report and Written Opinion of the ISA for PCT/IB2021/060552 mailed Feb. 16, 2022, 11 pages.

(Continued)

*Primary Examiner* — Christian Jang

(74) *Attorney, Agent, or Firm* — NIXON & VANDERHYE

(57) ABSTRACT

Apparatus for posturographic evaluation and for the therapeutic indication during a rehabilitation program of the systems involved in maintaining posture and balance of the patient, including two femoral accelerometer sensors installed on the thighs of the patient, a dorsal accelerometer sensor installed on the back in proximity to the D7 vertebra of the patient, held firmly in position by the restraint systems, an IOT platform whose surface has at least 16 load cells and in which the IOT platform includes a processing unit with internal processing circuit acquiring the output data from the load cells, from the two femoral accelerometer sensors and from the dorsal accelerometer sensor and sending the data to a central computer connected to an input device and to at least an output device and finally a dedicated (Continued)

software for the acquisition, analysis and processing of the input data for the real-time and post-processing uses.

20 Claims, 3 Drawing Sheets

(52) U.S. Cl.
CPC .......... *A61B 5/4023* (2013.01); *A61B 5/4561* (2013.01); *A61B 5/486* (2013.01); *A61B 5/6823* (2013.01); *A61B 5/6828* (2013.01); *A61B 5/6831* (2013.01); *A61B 5/6887* (2013.01); *A61B 5/7235* (2013.01); *A61B 5/002* (2013.01); *A61B 5/7405* (2013.01); *A61B 5/742* (2013.01); *A61B 5/7455* (2013.01); *A61B 2505/09* (2013.01); *A61B 2560/02* (2013.01); *A61B 2560/0406* (2013.01); *A61B 2560/0443* (2013.01); *A61B 2560/0468* (2013.01); *A61B 2562/0219* (2013.01); *A61B 2562/0252* (2013.01); *A61B 2562/046* (2013.01)

(56) References Cited

U.S. PATENT DOCUMENTS

| | | | | |
|---|---|---|---|---|
| 2004/0010202 | A1* | 1/2004 | Nakatani | A61B 5/113 600/529 |
| 2009/0281413 | A1* | 11/2009 | Boyden | A61B 5/412 600/407 |
| 2015/0018724 | A1 | 1/2015 | Hsu et al. | |
| 2019/0175078 | A1* | 6/2019 | Chen | A61B 5/1036 |

OTHER PUBLICATIONS

International Preliminary Report on Patentability (Chapter I of the Patent Cooperation Treaty) for PCT/IB2021/060552 mailed May 16, 2023, 9 pages.

* cited by examiner

POSTUROGRAPHIC EVALUATION APPARATUS AND METHOD

CROSS-REFERENCE TO RELATED APPLICATIONS

This application is the U.S. national phase of International Application No. PCT/IB2021/060552filed Nov. 15, 2021 which designated the U.S. and claims priority to IT patent application Ser. No. 102020000027774 filed Nov. 19, 2020, the entire contents of each of which are hereby incorporated by reference.

FIELD OF THE INVENTION

The present invention patent application generally refers to the medical branch of posturology and, more particularly, to a device for checking the correct posture of an individual in real time.

The invention is applicable to any field, where one such type of device can be advantageously used, but preferably this is aimed both for rehabilitating purposes and for preventive and diagnostic medicine.

STATE OF THE ART

As is known, posture is the spatial position of the human body as well as the relation between its body segments.

The capacity of an individual to maintain control of his/her own posture and to actively respond to internal and external perturbations, which test the balance, is a subject of clinical interest.

Postural stabilities varies in the course of life and depends on the level of maturity and functional integrity of the involved apparatuses. Indeed, start from birth and up to adolescence there is a phase of development and improvement of the capacities to maintain one's own body in balance, while in adult age these capacities encounter a physiological decline due to the reduction of efficiency of visual, vestibular and proprioceptive apparatuses.

Nevertheless, the postural stability can not only be correlated with the age-induced physiological decline but can also arise for various reasons. Modern life, full of comfort among chairs, couches, beds and too many hours stopped and seated, can play a decisive role in giving rise to a postural unbalance, which over time can become symptomatic and lead to symptoms from disturbances such as back pain, neck pain and shoulder pain, headache, breathing problems, rigidity and/or muscular atrophy, digestive problems, varicose veins and nerve compressions.

Not by chance, in recent years a great number of products and applications have been launched that are adapted to facilitate and assist the work of posture rehabilitation specialists, and in particular posturographic analysis has taken on an increasingly important role. Known also as posturography or stabilometry, posturographic analysis is the technique used for quantifying postural control in erect position in static or dynamic conditions.

Such applications range from the simplest to the most complex, but overall they are poorly adapted to the present needs, which require a method that is very effective but at the same time simple, practical and economically advantageous.

The simplest applications consist of the observation executed by the specialist during the execution of the patient rehabilitation exercises, evaluating the state and the progresses thereof. Nevertheless, such evaluations are subjective and subordinate to the inevitable imprecision to which human observation is subjected in the absence of specific measurement instruments. On the other hand, several aspects—even if quite relevant for diagnostic and clinical purposes—could be very difficult if not impossible to perceive.

Yet another different aspect are the measurements of the time and space parameters with the gait of the person, which provide important diagnostic and therapeutic information on the postural stability. Already known in the art are different types of systems for evaluating the correct posture of an individual, for example the stabilometric platforms or the electronic walkways of GAITRite and Vicon type, which represent the gold standard in the field and which—even if quite valid—are generally very costly, requiring considerable maintenance interventions and are hard to manage, since they require costly, spacious and high-quality deambulation laboratories. Therefore, the use for evaluating the correct posture of an individual at outpatient level, making use of said systems, is very limited at present.

On the contrary, the solutions based on inertia sensors like the accelerometers and the gyroscopes of IDF-235978-032 1 type, even if inexpensive, manageable and thus essentially easily implementable, are not very complete with respect to those attained with the aforesaid platforms. This involves an enormous limitation of the applicability of such technologies in the conventional configurations.

The present invention tends to reduce such limitations, by attaining—for the purpose of a postural stability detection—both a system that employs the data coming from a use of the stabilometric platforms and the data deriving from the use of the inertia sensors.

Hence, the main object of the present invention generally consists of making an apparatus capable of attaining a combined technique, due to which quantitative parameters are detected that can be easily interpreted by the professional and which describe the postural control of a person during the execution of state evaluations and which can be used in clinical and therapeutic diagnostics.

Another advantage ascribable to the present invention with respect to the prior art consists of the fact that it is easily and economically attainable on an industrial level, even using apparatuses and computer technologies that are already present on the market and widely validated in the art.

BRIEF DESCRIPTION OF THE INVENTION

With the present industrial invention patent application, it is intended to describe and claim a posturographic evaluation apparatus and method, provided with at least a new and alternative solution with respect to the solutions known up to now and in particular it is proposed to overcome one or more of the drawbacks or problems referred to above and/or to satisfy one or more of the needs perceived in the art and in particular inferable from that referred to above. The innovative concept underlying the present invention consists of having implemented a suitable measurement protocol aimed to acquire synchronized signals between an IOT platform and the inertia sensors applied on specific points of the body of the patient subjected to follow-up.

Specifically the present invention regards an apparatus capable of attaining a combined technique, due to which parameters are detected that can be easily interpreted by the professional and which describe the postural control of a person during the execution of state evaluations and which can be used clinical and therapeutic diagnostics.

For such purpose the inventors have attained an apparatus constituted by multiple devices capable of emitting, synchronizing and processing the output vector quantities from sensors interacting with the patient's body, so as to evaluate the incidence of particular pathological conditions, or to follow the evolution of a rehabilitation program of the systems involved in maintaining the posture and hence during the follow-up of the patient itself.

Said devices forming part of the innovative apparatus overall comprise three common accelerometers of triaxial type, an IOT platform provided with a processing unit with internal processing circuit capable of acquiring the output data from the three accelerometer sensors and from the load cells of the platform itself and of providing a first processing and then transmitting the data to the central computer, with a possible feedback unit as well as with at least an input device, with at least an output device and with a dedicated software for the acquisition, analysis and processing of the data detected for the real-time and post-processing uses.

A further objective is to propose an apparatus which is attainable on industrial scale, whose components are of standard type and perfectly retrievable on the market, and whose production is fully sustainable from an economical and environmental standpoint.

Other characteristics of the present invention are described in the following detailed description of one or more specific embodiments, protected by the various dependent claims.

BRIEF DESCRIPTION OF THE DRAWINGS

The preceding advantages, as well as other advantages and characteristics of the present invention, will be illustrated with reference to the enclosed figures, which are to be considered merely exemplifying and non-limiting or non-binding for the purposes of the present patent application, in which.

DETAILED DESCRIPTION OF THE INVENTION

The present invention will now be described in detail with reference to the figures and to a preferred embodiment thereof shown therein, in which identical reference numbers have been used for the same components.

Figure 1:
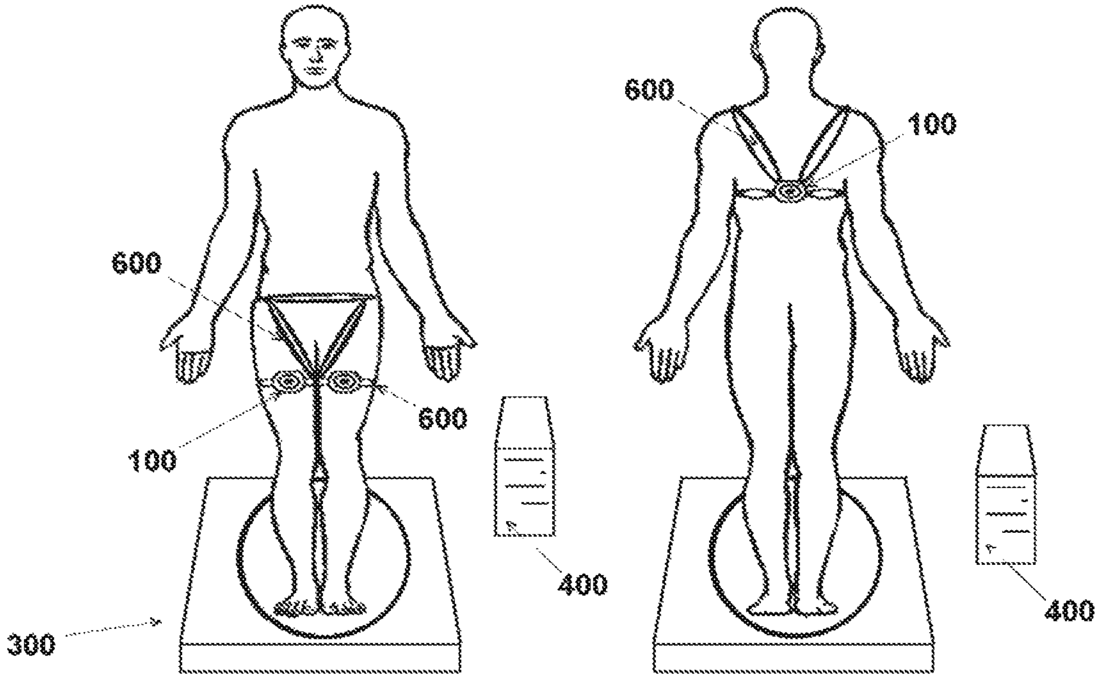
FIG. 1 is a perspective view of the central computer and front-dorsal view of the patient positioned on the IOT platform with three accelerometer sensors installed.

With reference to FIG. 1, this shows an apparatus for posturographic evaluation comprising multiple devices as described hereinbelow. Said devices are constituted by accelerometer sensors of triaxial type, in which the two femoral accelerometer sensors 100 installed on the thighs of the patient are maintained firmly in position by means of the restraint systems 600 and in which the dorsal accelerometer sensor 200, installed on the back in proximity to the D7 vertebra of the patient, is maintained firmly in position by means of the aforesaid restraint systems 600.

Figure 2:
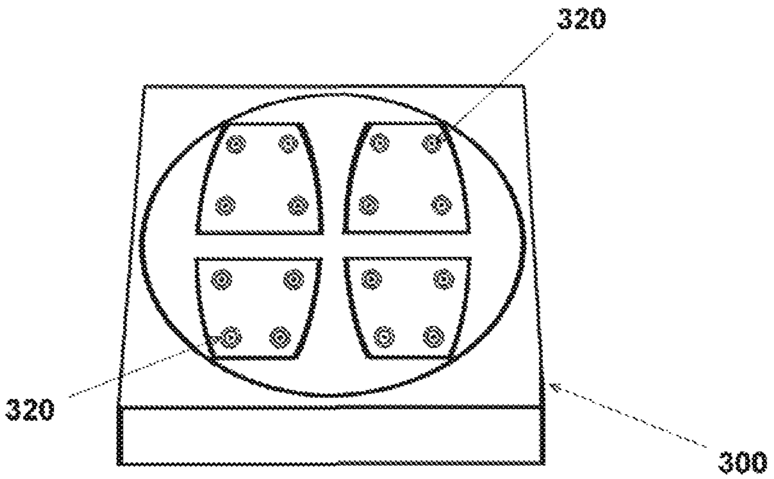
FIG. 2 is an axonometric view of the IOT platform.

As shown in FIGS. 1 and 2, said apparatus also comprises the IOT platform 300 on whose surface at least 16 load cells 320 are present. Said IOT platform 300 is also provided with a processing unit with internal processing circuit capable of acquiring the output data from the load cells 320 and from the two femoral accelerometer sensors 100 and from the dorsal accelerometer sensor 200, by means of wireless interconnection systems based on a standard comprising at least a protocol from among IEEE 802.11, IEEE 802.16, Bluetooth, GPRS and EDGE. In addition, the aforesaid IOT platform 300 provides for a first processing of all the aforesaid input data and then transmits it to the central computer 400 (FIG. 1) by means of at least a further aforesaid wireless interconnection system. Said central computer is also connected to at least an input device, such as a mouse, a keyboard, a microphone, a touchpad (not shown), to at least an output device, such as a common electronic display device (not shown). In addition, a dedicated software is provided for the acquisition, analysis and processing of the input data for the real-time and post-processing uses. An alternative embodiment of the present invention provides for the presence of a biofeedback unit (not shown) capable of interacting with the patient in a sensory manner.

A process is now described for operating the apparatus, object of the present invention, still with reference to an application that regards a patient subjected to follow-up.

Specifically, the two femoral accelerometer sensors 100 and the dorsal accelerometer sensor 200 are applied to the patient positioned above the IOT platform 300, by means of the restraint systems 600. Then, the patient is made to simulate a stationary walking on said IOT platform 300, for a period comprised between 3 min and 10 min, in a manner such that the femoral 100 and dorsal 200 accelerometer sensors and the load cells 320 detect the movements in the form of vector quantities.

Said output data is sent to the processing unit of the IOT platform 300, which will be able to provide for a first processing and then transmit the data to the central computer 400, which will process it by means of the suitable software.

Figure 3:
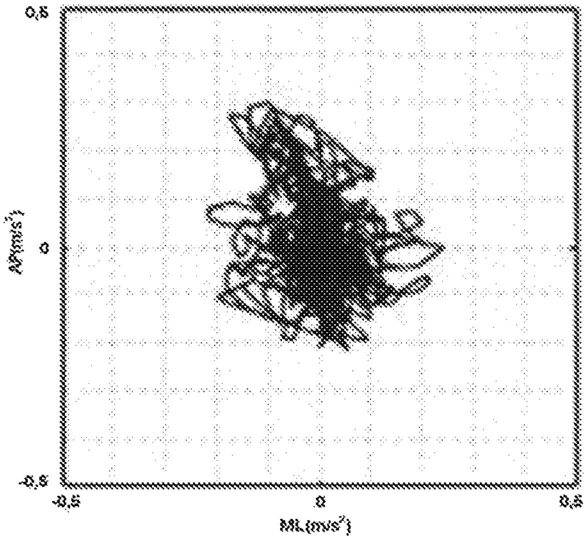
FIG. 3 is an exemplifying diagram of the output data from the accelerometer sensors in the anteroposterior plane (AP) and mediolateral plane (ML) detected on a healthy patient.

Specifically, already from the simple data coming from the femoral 100 and dorsal 200 accelerometer sensors it is possible to obtain parameters capable of extracting useful information on the stability of the person subjected to the stabilometric exam and in particular on the mode with which the energy of the movements is expressed over time. Indeed, from the analysis of the different frequencies that constitute the acceleration wave of the three sensors, important relations are detected between the movements of the trunk and those of the lower limbs. As is shown in FIG. 3, where the acceleration signal values in the anteroposterior plane (AP) and mediolateral plane (ML) of a healthy subject are reported, a prevalence of low or medium-low acceleration values will indicate uniformity and balance, while a prevalence of high acceleration values will indicate imbalance.

Figure 4:
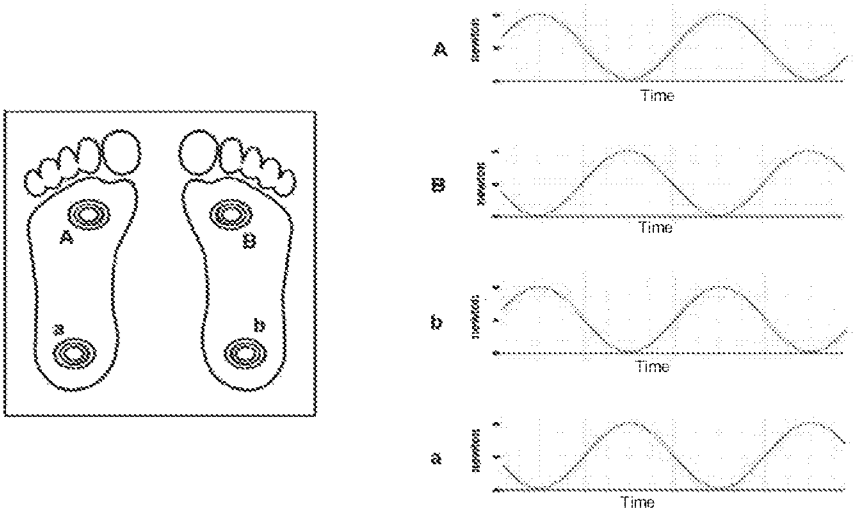
FIG. 4 is a diagram of the output data detected on a healthy patient and coming from the pressure cells of the IOT platform expressed as a function of the activation of each load cell.

As in the case of accelerometers, also from the signals detected by the IOT platform 300, by means of the load cells 320, it is possible to obtain further useful information regarding the stability of the patient subjected to follow-up. In particular, as shown in FIG. 4, by means of the stationary walking, the movement will be alternately obtained of the weight on the front of the right foot and on the rear of the foot and vice versa, on each load cell giving rise to pressures represented by sinusoidal waveforms offset with 4 groups of 180°. The evaluation of the uniformity of the movement can be carried out by means of the dedicated software, by comparing the waveforms after having canceled the phase shift thereof. The execution of one such procedure on a fixed number of periods allows calculating a "homogeneity index", which provides an objective evaluation of the capacity of the patient to maintain continuous and uniform movement modes.

In addition, in order to obtain an even more validated metrological evaluation of the mechanisms due to which a person is capable of controlling posture and balance, it is possible to provide the detection of the force imparted on the load cells 320, obtaining a "residual deficit index in rehabilitation" which, combined with the standardized stabilometric algorithms, will be able to restore also in feedback mode the resistance to the motor action of the user, and thus with the main goal of recovering or correcting the aforesaid force thereof.

A fundamental objective of the present invention consists of carrying out, by means of the dedicated software, an integration between the values of the acceleration data detected by the three aforesaid femoral 100 and dorsal 200 accelerometer sensors and the indices of homogeneity and residual deficit, obtained from the IOT platform 300, allowing the obtainment of a postural and balance evaluation of the body of the patient subjected to the follow-up, by means of a dedicated interface of the system observable directly and easily by the professional and thus so as to evaluate both the incidence of particular pathological conditions and to follow the evolution of a rehabilitation program of the systems involved in maintaining the posture and thus during the follow-up of the patient subjected to the examination.

Such method in reality is fundamental for inventive purposes, since it allows showing, on an interface, the integrated values coming from two specific techniques, i.e. techniques which on one hand make use of the data detected by the inertia sensors and on the other hand of the data detected by the stabilometric platforms. Even if each of these techniques have been well validated, nevertheless together they provide unequivocal data that is easily comprehensible by a man skilled in the art by means of the observation of the user interface of the dedicated software.

Figure 5:
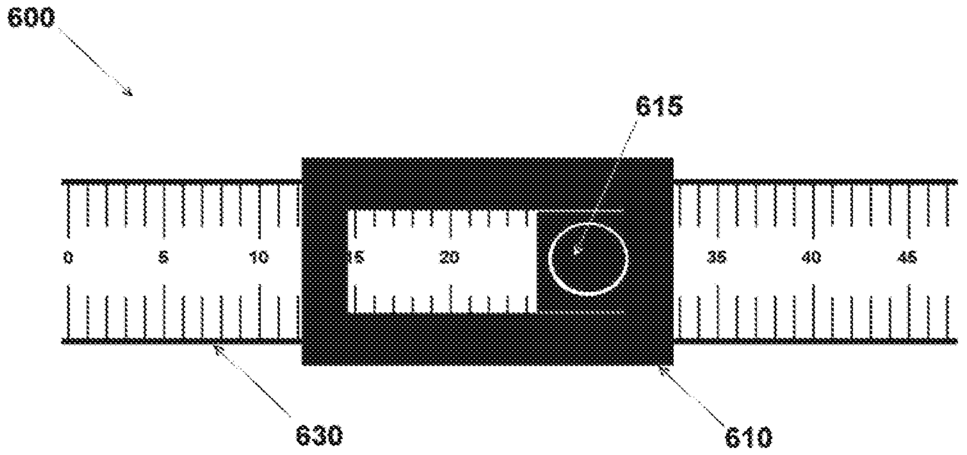
FIG. 5 is a front view of the restraint system of the accelerometers.

A further aspect, alongside all the technical solutions described up to now, but of particular relevance for the attainment of the invention, is that how—already partly described in those cases where one seeks a cooperation by the patient—it provided that the apparatus, object of the present invention, can also constitute a valid instrument of biofeedback for the patient. Specifically, the software program can be configured in order to provide biofeedback by means of a real-time user posture interface, advantageously in order to warn him/her during the stationary walking step that he/she has a totally unstable posture or that it is unstable only during several steps of the movement or that he/she must recover or correct the aforesaid force thereof applied on the IOT platform. By way of example, the biofeedback could be obtained by means of vibration (e.g. stimulation or vibration of the platform or of the sensors), by means of viewing (e.g. presenting the integrated data at the visual field of the person, on a telephone, a display, a series of light sources), by means of hearing (e.g. sounds perceived directly or by means of headphones or ear pieces), by means of temperature (e.g. at the feet or elsewhere), by means of other sensory mechanisms (e.g. a tactile mechanism) or any combination thereof. Another characteristic, which even if complementary is fundamental for the purpose of a correct attainment of the invention, consists of the fact that the restraint systems 600 of the femoral 100 and dorsal 200 accelerometer sensors are suitably designed so as to keep said sensors perfectly adherent to the body of the patient and thus so as to eliminate all the artifacts that could inexorably falsify the correct detection of the output data. For such purpose, with reference to FIG. 5, said restraint systems 600 are constituted by a belt 630 made of technical material, such as nylon and cotton, adjustable for sliding in a buckle 610 with quick snap-lock closure by means of the locking button 615, in order to ensure an optimal hold of the position for the entire duration of the detection. In addition, in order to allow a correct tightening of said restraint system 600 on the portion of the belt 630, which corresponds to the section passing through the buckle 610, a graduated scale is inventively traced, which allows maintaining an adjustment that is respectively uniform and personalized for use by each specific patient.

In conclusion, it is important to focus attention on the fact that the parameters that the apparatus provides, as well as the interpretation criteria of the same have the object of allowing the clinician not only to recognize and quantify the possible balance and postural deficit, but also to identify in the results the indications for a possible diagnostic and therapeutic investigation. In other words, a fundamental innovative characteristic of the inventive apparatus lies not only in a simple diagnostic evaluation but also in the therapeutic capacity integrated with the evaluation itself and hence allows evaluating the incidence of particular pathological conditions or of following the evolution of a rehabilitation program of the systems involved in maintaining the posture and hence during the follow-up of the patient.

Further characteristic of the present invention consists of the fact that the aforesaid acquired data relative to each patient will be, due to the aforesaid dedicated software, stored, managed and retrieved by a specific storage infrastructure, such as big data or cloud data for each pathology class. The aforesaid data may possibly be advantageously introduced in the scope of the "Research and Development" field present in the medical field.

Of course the data provided herein is merely exemplifying and absolutely non-limiting for the purpose of the scope of the present invention, since it only serves for allowing a man skilled in the art to comprehend several possible applications and embodiments of the finding. Then, different obvious modifications could be clearly made by the average person skilled in the art to the preceding exemplifying and non-limiting embodiments described with reference to the figures, without this involving an extension beyond the inventive concept which underlies the present invention, as defined by the following dependent claims.

The invention claimed is:

1. A posturographic evaluation apparatus comprising:

two femoral accelerometer sensors configured to be respectively installed on each thigh of a patient and held firmly in place by a set of first restraint systems, the two femoral accelerometer sensors outputting a set of first input data;

a dorsal accelerometer sensor configured to be installed on a back of the patient and held firmly in place by a second restraint system, the dorsal accelerometer outputting second input data;

an Internet of Things (IOT) platform having a surface that has at least 16 load cells separated into four sets of the load cells corresponding to a front left foot, a rear left foot, a front right foot, and a rear right foot, the load cells being configured to output third input data as sinusoidal waveforms offset with four groups of 180° upon input of a movement on the at least 16 load cells, said IOT platform comprising a processor with an internal processing system configured to process the set of first input data, the second input data, and the third input data received from the two femoral accelerometer sensors, the dorsal accelerometer sensor, and the load cells, the set of first input data and the second input data from the two femoral accelerometer sensors and the dorsal accelerometer sensor being used to obtain acceleration signal values in the anteroposterior plane and the mediolateral plane of the patient, the sinusoidal waveforms of the third input data being compared to determine whether the movement is uniform; and a central computer connected to said processor of the IOT platform, at least an input device, and at least an output device, the central computer comprising dedicated software to acquire, analyze, and process the acceleration signal values and the sinusoidal waveforms for real-time and post-processing uses to detect postural stability of the patient.

2. The posturographic evaluation apparatus according to claim 1, further comprising a biofeedback system configured to interact with the patient by sensory mechanisms comprising at least one of vibration, vision, hearing, and temperature.

3. The posturographic evaluation apparatus according to claim 2, wherein said IOT platform provides for a first processing of all the input data from the two femoral accelerometer sensors, the dorsal accelerometer sensor, and the load cells, and wherein the processed data are subsequently transmitted to the central computer.

4. The posturographic evaluation apparatus according to claim 2, wherein both the connection between the femoral accelerometer sensors and the dorsal accelerometer sensor with the processor of the IOT platform and the connection between said processor of the IOT platform and the central computer occurs by wireless interconnection systems based on a standard comprising at least one protocol from IEEE 802.11, IEEE 802.16, Bluetooth, GPRS, and EDGE.

5. The posturographic evaluation apparatus according to claim 2, wherein said input device comprises at least one of a mouse, a keyboard, a microphone, and a touchpad, and wherein said output device comprises a common electronic display device.

6. The posturographic evaluation apparatus according to claim 2, wherein said dedicated software is configured to show on a single interface the data values detected by the femoral and dorsal accelerometer sensors integrated with the data values detected by the load cells of the IOT platform, and wherein said software stores, manages and retrieves said data values in a specific storage infrastructure and big data or cloud data for each pathology class related to the patient using the apparatus.

7. The posturographic evaluation apparatus according to claim 1, wherein said IOT platform provides for a first processing of all the input data from the two femoral accelerometer sensors, the dorsal accelerometer sensor, and the load cells, and wherein the processed data are subsequently transmitted to the central computer.

8. The posturographic evaluation apparatus according to claim 7, wherein both the connection between the femoral accelerometer sensors and the dorsal accelerometer sensor with the processor of the IOT platform and the connection between said processor of the IOT platform and the central computer occurs by wireless interconnection systems based on a standard comprising at least one protocol from IEEE 802.11, IEEE 802.16, Bluetooth, GPRS, and EDGE.

9. The posturographic evaluation apparatus according to claim 3, wherein said input device comprises at least one of a mouse, a keyboard, a microphone, and a touchpad, and wherein said output device comprises a common electronic display device.

10. The posturographic evaluation apparatus according to claim 7, wherein said dedicated software is configured to show on a single interface the data values detected by the femoral and dorsal accelerometer sensors integrated with the data values detected by the load cells of the IOT platform, and wherein said software stores, manages and retrieves said data values in a specific storage infrastructure and big data or cloud data for each pathology class related to the patient using the apparatus.

11. The posturographic evaluation apparatus according to claim 1, wherein both the connection between the femoral accelerometer sensors and the dorsal accelerometer sensor with the processor of the IOT platform and the connection between said processor of the IOT platform and the central computer occurs by wireless interconnection systems based on a standard comprising at least one protocol from IEEE 802.11, IEEE 802.16, Bluetooth, GPRS, and EDGE.

12. The posturographic evaluation apparatus according to claim 11, wherein said input device comprises at least one of a mouse, a keyboard, a microphone, and a touchpad, and wherein said output device comprises a common electronic display device.

13. The posturographic evaluation apparatus according to claim 4, wherein said dedicated software is configured to show on a single interface the data values detected by the femoral and dorsal accelerometer sensors integrated with the data values detected by the load cells of the IOT platform, and wherein said software stores, manages and retrieves said data values in a specific storage infrastructure and big data or cloud data for each pathology class related to the patient using the apparatus.

14. The posturographic evaluation apparatus according to claim 1, wherein said input device comprises at least one of a mouse, a keyboard, a microphone, and a touchpad, and wherein said output device comprises a common electronic display device.

15. The posturographic evaluation apparatus according to claim 1, wherein said dedicated software is configured to show on a single interface the data values detected by the femoral and dorsal accelerometer sensors integrated with the data values detected by the load cells of the IOT platform, and wherein said software stores, manages and retrieves said data values in a specific storage infrastructure and big data or cloud data for each pathology class related to the patient using the apparatus.

16. The posturographic evaluation apparatus according to claim 1, wherein said restraint systems of the femoral and dorsal accelerometer sensors are configured to keep said sensors perfectly adherent to the body of the patient, by a belt of technical material, nylon, and cotton, wherein said belt is adjustable by sliding in a buckle with a quick snap-lock closure by the locking button, and wherein a graduated scale is traced on the belt portion, which corresponds to the end section passing through the buckle.

17. A posturographic evaluation method, comprising:

applying two femoral accelerometer sensors to thighs of a patient positioned above an Internet of Things (IOT) platform, the two femoral accelerometer sensors being locked in position by a first set of restraint system;

applying the dorsal accelerometer sensor to a back of the patient near the D7 vertebra of the patient, the dorsal accelerometer sensor being locked in position by a second restraint system;

receiving, on the Internet of Things (IOT) platform having a surface that has at least 16 load cells separated into four sets of the load cells corresponding to a front left foot, a rear left foot, a front right foot, and a rear right foot, the load cells being configured to output data as sinusoidal waveforms offset with four groups of 180° upon input of a movement on the at least 16 load cells, an input related to a movement of the patient simulating stationary walking on the IOT platform for a period between 3 min and 10 min;

detecting, by the two femoral accelerometer sensors, the dorsal accelerometer sensor, and the load cells of said IOT platform, the movements in a form of vector quantities;

sending the detected vector quantities to a processor of the IOT platform in a form of data;

processing, at the processor of the IOT platform, the data;

transmitting the processed data to a central computer; and using dedicated software to additionally process the transmitted data, wherein the vector quantities are used to obtain acceleration signal values in the anteroposterior plane and the mediolateral plane of the patient, the sinusoidal waveforms are compared to determine whether the movement is uniform, and the acceleration signal values and the sinusoidal waveforms are processed to detect postural stability of the patient.

18. The posturographic evaluation method according to claim 17, wherein said dedicated software detects the postural evaluation of the body of the patient by a dedicated system interface observable by a technician, enabling the technician to evaluate both an incidence of particular pathological conditions and following the evolution a rehabilitation program of the systems involved in maintaining posture and balance.

19. The posturographic evaluation method according to claim 18, wherein said dedicated software program is configured to provide biofeedback by a real-time user posture interface to alert the user during the stationary walking step that the user has totally unstable posture or is unstable only during some phases of the movement.

20. The posturographic evaluation method according to claim 17, wherein said dedicated software program is configured to provide biofeedback by a real-time user posture interface to alert the user during the stationary walking step that the patient has totally unstable posture or is unstable only during some phases of the movement.

* * * * *